US010646109B1

(12) United States Patent
Freeman et al.

(10) Patent No.: US 10,646,109 B1
(45) Date of Patent: May 12, 2020

(54) DEVICE AND METHOD OF BALLOON ENDOSCOPY

(75) Inventors: Jenny E. Freeman, Weston, MA (US); Derek Brand, Somerville, MA (US); Michael J. Hopmeier, Mary Esther, FL (US)

(73) Assignee: HYPERMED IMAGING, INC., Memphis, TN (US)

( * ) Notice: Subject to any disclaimer, the term of this patent is extended or adjusted under 35 U.S.C. 154(b) by 1027 days.

(21) Appl. No.: 11/184,082

(22) Filed: Jul. 19, 2005

Related U.S. Application Data

(60) Provisional application No. 60/588,801, filed on Jul. 19, 2004.

(51) Int. Cl.
| A61B 1/00 | (2006.01) |
| A61B 1/06 | (2006.01) |
| A61B 1/04 | (2006.01) |

(52) U.S. Cl.
CPC .......... *A61B 1/041* (2013.01); *A61B 1/00082* (2013.01); *A61B 1/00154* (2013.01)

(58) Field of Classification Search
CPC .................................................. A61B 1/041
USPC ........ 600/102, 114–116, 121, 129, 175, 103, 600/117, 118, 160, 178
See application file for complete search history.

(56) References Cited

U.S. PATENT DOCUMENTS

| 4,517,979 | A | * | 5/1985 | Pecenka | 606/195 |
| 4,961,738 | A | * | 10/1990 | Mackin | 606/15 |
| 4,976,710 | A | * | 12/1990 | Mackin | 606/15 |
| 5,152,277 | A | * | 10/1992 | Honda et al. | 600/116 |
| 5,749,883 | A | * | 5/1998 | Halpern | 606/159 |
| 5,904,648 | A | * | 5/1999 | Arndt et al. | 600/120 |
| 5,984,860 | A | * | 11/1999 | Shan | 600/116 |
| 6,240,312 | B1 | * | 5/2001 | Alfano | A61B 1/00016 128/903 |
| 6,658,279 | B2 | * | 12/2003 | Swanson et al. | 600/407 |
| 6,709,388 | B1 | * | 3/2004 | Mosse et al. | 600/114 |
| 7,721,742 | B2 | * | 5/2010 | Kalloo et al. | 600/115 |
| 2003/0114742 | A1 | * | 6/2003 | Lewkowicz et al. | 600/407 |
| 2003/0216622 | A1 | * | 11/2003 | Meron et al. | 600/300 |
| 2003/0225370 | A1 | * | 12/2003 | Mueller | 604/106 |
| 2004/0111019 | A1 | * | 6/2004 | Long | 600/407 |
| 2004/0122417 | A1 | * | 6/2004 | Rabiner et al. | 604/528 |
| 2004/0162469 | A1 | * | 8/2004 | Imran | 600/310 |

(Continued)

*Primary Examiner* — Alexandra L Newton
*Assistant Examiner* — Rynae Boler
(74) *Attorney, Agent, or Firm* — Brett A. Lovejoy; Andrew J. Antczak; Morgan, Lewis & Bockius LLP (57) ABSTRACT

A medical device is provided that comprises: (i) an expandable capsule that can be swallowed by a patient and positioned to a target tissue within the patient, (ii) an endoscope attached to the capsule for obtaining an image of the target tissue at a wavelength of interest, and (iii) a thin tube or wire configured to position the device to the target tissue. The thin tube or wire is expandable. The capsule can be swallowed in stages to position the device at different locations within the gastrointestinal tract. The thin tube or wire can deliver electromagnetic radiation for visualization of the target tissue. The thin tube or wire can provide a passage of a biopsy device for access to the target tissue. In some instances, the capsule comprises a band which rotates around the capsule to clean the capsule. In some instances, the capsule collects multispectral or hyperspectral information.

19 Claims, 6 Drawing Sheets

(56) References Cited

U.S. PATENT DOCUMENTS

| | | |
|---|---|---|
| 2004/0236414 A1* | 11/2004 | Brar et al. .................... 623/1.42 |
| 2005/0124875 A1* | 6/2005 | Kawano et al. .............. 600/407 |
| 2005/0215911 A1* | 9/2005 | Alfano ................... A61B 1/041 |
| | | 600/476 |
| 2005/0222496 A1* | 10/2005 | Sekiguchi ..................... 600/115 |
| 2005/0222500 A1* | 10/2005 | Itoi .............................. 600/180 |
| 2005/0245788 A1* | 11/2005 | Gerber .......................... 600/115 |
| 2006/0009758 A1* | 1/2006 | Edwards et al. ................ 606/41 |
| 2006/0241345 A1* | 10/2006 | Oishi et al. ................... 600/116 |

* cited by examiner

- Tethers are both attached to rings which can rotate independently of the balloon.
- Rotation of the scope will impact the tethers (which can be semi-rigid) and will cause them to rotate with the scope.
- Because the head of the scope is beyond the tethers, they are never directly in the field of view.
- This allows the balloon to remain stable and be independent of the twisting and rotation of the scope.

Rings allow scope to rotate without moving balloon

DEVICE AND METHOD OF BALLOON ENDOSCOPY

REFERENCE TO RELATED APPLICATIONS

This invention claims priority to U.S. Provisional Application No. 60/588,801 entitled "Device and Method of Balloon Endoscopy" filed Jul. 19, 2004, which is specifically and entirely incorporated by reference.

BACKGROUND

1. Field of the Invention

This invention is directed to devices and methods for performing balloon endoscopy.

2. Description of the Background

Numerous minimally-invasive diagnostic and treatment devices and methods of using them have been developed. Two such categories of devices are endoscopes and balloon catheters.

Endoscopes have proved useful in the examination of internal surfaces, in connection with various surgical and diagnostic procedures. However, conventional endoscopes, such as colonoscopes, gastroscopes, bronchoscopes, and angioscopes, are limited in their ability to detect all pathology present or provide unequivocal identification of abnormalities. These devices typically collect reflected visible light from a lumen, which may be expanded with water or gas, for simple visual evaluation of the tissue surface of interest. If a definitive diagnosis of the type of pathology or disease present in the tissue is needed, a tissue specimen is typically removed or biopsied and submitted for pathologic testing. Unfortunately, the biopsy process increases the risk of complications to the patient, such as hemorrhage, infection, and possible perforation of the organ or vessel under examination.

In addition to endoscopic devices that collect reflected visible light to produce an image allowing for simple visual evaluation, endoscopes that detect fluorescence emitted following excitation of tissue with a radiation source have also been described. One such device includes a visible light source, an optional endoscopic probe, optical sensors, a filter, a detector, and a display monitor. One or two wavelengths of visible light, preferably blue and red/near-infrared light, is directed to the tissue of interest, and remittance and autofluorescence is then detected, integrated/processed and displayed (U.S. Pat. No. 5,590,660 to MacAulay). This device does not incorporate balloons into the probes to facilitate optical coupling, or to allow visible light or infrared-based evaluation of the diseased tissue.

Another device, useful for diagnosing the condition of GI tissue, utilizes fiber optics to detect emitted fluorescence following excitation radiation treatment (U.S. Pat. No. 5,421,337 to Richards-Kortum). In addition, devices which detect precancerous lesions using a mercury arc lamp endoscope (U.S. Pat. No. 5,647,368 to Zeng), devices which monitor and determine pre-existing physical properties of an organ by excitation with UV light (U.S. Pat. No. 5,456,252 to Vari), and devices which determine bilirubin concentration in tissue using reflectance spectroscopy (U.S. Pat. No. 5,353,790 to Jacques) have also been described. However, these devices do not combine balloon endoscopes with infrared radiation to detect diseased tissue.

Balloon catheters, like endoscopes, have been routinely used for diagnostics and treatment. Typical uses of conventional balloon catheters include procedures such as angioplasty and embolectomy. However, these conventional balloon devices can not be used in procedures in which infrared light is emitted in close proximity or directly onto a tissue surface, followed by collection of the light reflected or emitted from the tissue of interest, due to moisture and fluids in the surrounding environment.

The use of infrared and most ranges of radiation in catheters and endoscopic devices is complicated by the fact that water and most bodily fluids (notably blood and stool) are opaque to infrared light and visible light as well. Blood or stool impairs collection of light at any wavelength. Consequently, even the slightest amount of moisture on the collection end of an endoscopic probe impairs the collection of infrared light. As a result, conventional endoscopes and balloon catheters cannot be used in infrared procedures where moisture or bodily fluids are present. In the visible range, folds in the wall, tethering of the intestine or other features may prohibit optimal visualization. Although insufflation of the gut will distend and display the wall, the process causes pain and discomfort to the patient.

Fiber optic laser catheters and endoscopes having a protective shield over the probe tip have been described as useful in connection with the diagnosis and removal of atherosclerosis. In one such device, an optical fiber(s) carrying laser radiation is mounted in a catheter having a transparent protective optical shield over its distal end (U.S. Pat. Nos. 5,318,024 and 5,125,404 to Kittrell). The fiber(s) is anchored within the catheter so that there is an appropriate distance or space between the output end of the fiber(s) and the tip of the shield. The intervening space may be filled with fluid, optical surfaces may be optically contacted, or they may be anti-reflection coated to reduce reflections and maximize transmitted light. The catheter may be inserted into a blood vessel and the shield brought into contact with a plaque or obstruction site.

In this device, the protective optical shield mechanically displaces blood at the region to be analyzed and also protects the distal tip of the optical fiber(s) from intra-arterial contents. By locally displacing blood, the shield allows viewing of the tissue of interest without the need for a purge or flush. The optical shield may be in the form of glass, fused silica, sapphire or other optically transparent material. A flexible balloon over the tip of the probe may also be used as an optical shield. A different balloon may be used to provide an anchor point for positioning the catheter during use.

Although the shields of these devices protect a probe tip from blood contaminants, the use of a single balloon to both anchor and protect the tip of the probe from infrared opaque contaminants, which simultaneously allows optical coupling in the infrared region between the probe tip and the tissue surface, has not previously been described. The Kittrel devices are designed for use with visible light. In addition, probes incorporating two anchoring balloons which allow the evacuation of a lumen and its subsequent filling with an infrared lucent coupling fluid are also not described.

Because of the challenges posed by the effect of moisture on infrared light and opaque bodily fluids to all light transmission, available endoscopic devices and catheters are limited in their ability to access and evaluate tissue and/or the lumen of vessels and organs using infrared light. There is therefore a need for a relatively non-invasive device which allows for optical coupling of a probe to the tissue or surface of interest, thereby allowing thorough evaluation and diagnosis of tissues and/or the lumen of vessels and organs using visible, ultraviolet or infrared radiation.

SUMMARY

The present invention overcomes the problems and disadvantages associated with current strategies and designs and provides new devices and methods for performing balloon endoscopy.

One embodiment of the invention is directed to medical devices comprising a catheter for insertion of the medical device into the body of a patient; an endoscope attached to said catheter for obtaining an image of a target tissue within said body at a wavelength of interest; and a balloon attached to the catheter, wherein said balloon is translucent to said wavelength. Preferably, the catheter is flexible and allows for positioning of the device within the patient, and expansion of the balloon stabilizes positioning of the endoscope to image the target tissue. The balloon may be expanded by filling with a fluid that is translucent to the wavelength of interest, which may be in the range of infrared, near infrared, visible or ultraviolet light. Medical devices of the invention may be used for data collection, such as for hyperspectral or multispectral imaging of a target tissue of interest, or for treatment of the patient by administering radiation, drugs or other medical treatment to the diseased or damaged tissue.

The device may further comprise a band that is capable of rotating around said balloon for treating the surface of the balloon or the target tissue. The device may be attached to a camera for imaging and recording images of the tissue both before and after treatment.

Another embodiment of the invention is directed to medical devices comprising a capsule that can be swallowed by a patient and positioned to a target tissue. An endoscope is attached to said capsule, and may further comprises a thin tube or wire to position said device to said target tissue. Preferably the thin tube or wire is expandable, and the capsule may be swallowed in stages to position said device at different locations within the gastrointestinal tract.

Another embodiment of the invention is directed to methods for positioning an endoscope with a patient comprising administering the medical devices of the invention. Devices may be positioned with catheters or wires, or simply swallowed. Preferably, the device is maintained within the target tissue of interest and stably and repeatedly maintained. The tissue of interest may be expanded or manipulated for better visualization or uniform data collection without the need for insufflation, or the balloon may be inflated for stabilization or better visualization of the target tissue.

Other embodiments and advantages of the invention are set forth in part in the description, which follows, and in part, may be obvious from this description, or may be learned from the practice of the invention.

DESCRIPTION OF THE INVENTION

Balloon endoscopes are routinely used for diagnostics and treatment. Typical uses of conventional balloon catheters include procedures such as angioplasty and embolectomy. However, these conventional balloon devices can not be used in procedures in which infrared light is emitted in close proximity or directly onto a tissue surface, followed by collection of the light reflected or emitted from the tissue of interest, due to moisture and fluids in the surrounding environment. Also, at least in part because of the challenges posed by the effect of moisture on infrared light and opaque bodily fluids to all light transmission, available endoscopic devices are limited in their ability to access and evaluate tissue and/or the lumen of vessels and organs using infrared light.

A relatively (matched with conventional devices and methods) non-invasive endoscopic device has been surprisingly discovered that allows for optical coupling of a probe to the tissue or surface of interest, thereby allowing thorough evaluation and diagnosis of tissues and/or the lumen of vessels and organs. Preferred electromagnetic wavelength ranges include, but are not limited to, visible, ultraviolet or infrared radiation.

In one embodiment of the invention, the endoscope comprises a balloon that is lucent to the wavelengths being collected either as a part of a catheter which is introduced into the mouth or nose of a patient or on a capsule that is swallowed. Such a capsule may be totally free of any attachment or may be attached to a string or thin tubular structure which provides the capabilities to control the position of the capsule in the esophagus, maintains the position of the capsule at a particular site of interest, or is used to inflate the balloon, to deliver light for visualization or illumination of the esophagus or provides for passage of a biopsy device through a hole in the distal end. These wavelengths include, but are not limited to, visible, infrared, or ultraviolet and the process may include collection of fluorescence data.

The balloon is preferably composed of an inert material that allows for transmission of visible, infrared, near infrared, or fluorescent radiation, and may be useful to support the surface under investigation. Balloons may also be porous or able to be punctured at one or more locations along their surface. Preferably, balloon size is pre-determine to the size of the cavity or area being investigated. In addition, balloons may be infused with a drug or other substance to be transferred to the area of interest, or simply used as a mechanism to spread such substances evenly over a target area. The collection of spectral, hyperspectral or multispectral information from the site could be used to determine the dose and or type of substance administered. The balloon may be expanded or dilated to pass through or to lodge the device at certain locations within the body. For example, the balloon may be expanded or dilated at joints to lodge the devise for data collection and/or the administration of treatment. Alternatively, an expanded balloon may be constricted to allow the device to pass through a stricture or narrow passage of a target tissue or organ.

Another embodiment of the invention is directed to a balloon endoscope wherein the balloon is lucent to the wavelengths being collected, and is a part of a catheter which is introduced into the mouth or nose of a patient, or is a part of a capsule that is swallowed. The capsule may be totally free of any attachment or may be attached to a string or thin tubular structure that controls the position of the capsule in the esophagus and maintains position of the capsule at a particular site of interest. The endoscope or catheter may be used to inflate the balloon and deliver light for visualization or illumination of the esophagus or allow for passage of a biopsy device through a hole in the distal end. Useful wavelengths include visible, infrared, or ultraviolet and include collection of fluorescence data. Embodiment of the invention may be used in areas of the body such as, but not limited to, regions of the gastrointestinal tract (e.g. stomach, intestines, esophagus), the bladder, regions of the blood system (e.g. heart, veins, arteries), sinuses and any cavity of the body, whether accessible from the exterior or requiring internal placement by surgery or simple insertion. As an additional feature, the balloon may also assist in stabilizing the surfaces it comes in contact with and/or the surfaces being investigated.

Another embodiment of the invention is directed to a capsule on a string with no balloon. Such a capsule is swallowed as opposed to a tube or endoscope that was pushed through the mouth or nose and into the esophagus or stomach. Inflation provides visualization of organs with larger lumens such as colon. This is different from current capsules used for endoscopy in that it is attached to a small tube or tether that serves to control the position of the capsule upon and permit the maintenance of the capsule in a particular location of interest over the duration of many swallows or propulsive events. This tube or tether also provides the capabilities for biopsy or suction of secretions either proximal or distal to the capsule, to irrigate with saline to wash the lumen wall and/or balloon and to provide a way to control a small band which can rotate around the balloon to clean its surface if necessary.

Another embodiment of the invention is directed to a method of advancing the balloon catheter into the stomach. In an embodiment, the balloon catheter is attached to a semi-rigid tube and advanced by the individual performing the procedure through the nose or mouth. In another embodiment, the device may be attached to a floppy or flexible tube, and the end of the tube with the balloon catheter is swallowed by the patient to advance the device into the stomach.

Another embodiment of the invention is directed to a method for inflating the balloon catheter with a fluid which is transparent to (A) near-infrared light, (B) infrared light, (C) visible light, and/or (D) ultraviolet light, where near infrared light is light with a wavelength between 700 nm and 1100 nm, infrared light is light with a wavelength between 1100 nm and 5000 nm, visible light is light with a wavelength between 400 nm and 700 nm, and ultraviolet light is light with a wavelength between 200 nm and 400 nm. Fluids that are translucent to these wavelengths are well know to those skilled in the art and may be gasses or liquids. These fluids include, but are not limited to, water, water vapor, noble gasses, carbon dioxide, nitrogen, oxygen, helium, hydrogen, argon, boron and mixtures thereof. Preferably, the fluids are non-toxic and harmless to the patient.

Another embodiment of the invention is directed to method of detecting light either via fibers in contact with the walls of the balloon or via a detection system similar to that on a traditional endoscope or capsule. Any of a variety of CCD, CMOS or other detectors may be used within the capsule or at the end of collecting fibers. Collection optics may include a variety of lenses including wide angle. The lens may be a part of the balloon wall or the balloon may be a part of the lens.

In another embodiment, a capsule on a string with no balloon would be a capsule that was swallowed as opposed to a tube or endoscope that was pushed through the mouth or nose and into the esophagus or stomach. This is different from current capsules used for endoscopy in that it is attached to a small tube or tether which serves to control the position of the capsule upon and permit the maintenance of the capsule in a particular location of interest over the duration of many swallows or propulsive events. This tube or tether also provides the capabilities for biopsy or suction of secretions either proximal or distal to the capsule.

Another embodiment of the invention comprises a method of advancing the balloon catheter into the stomach. In one embodiment of the device, the balloon catheter is attached to a semi-rigid tube and advanced by the individual performing the procedure through the nose or mouth. In a second embodiment, the device is attached to a floppy or flexible tube, and the end of the tube with the balloon catheter is swallowed by the patient to advance the device into the stomach.

A method for inflating the balloon catheter with a fluid which is preferably transparent to (A) near-infrared light, (B) infrared light, (C) visible light, and (D) ultraviolet light, where near infrared light is light with a wavelength between 700 nm and 1100 nm, infrared light is light with a wavelength between 1100 nm and 5000 nm, visible light is light with a wavelength between 400 nm and 700 nm, and ultraviolet light is light with a wavelength between 200 nm and 400 nm.

Light can be detected either via fibers in contact with the walls of the balloon or via a detection system similar to that on a traditional endoscope or capsule. Any of a variety of CCD, CMOS or other detectors may be used within the capsule or at the end of collecting fibers. Collection optics may include a variety of lenses and multiple lenses pointing in multiple directions including wide angle, the lens as part of the balloon wall, or the balloon is part of the lens.

Figure 1:
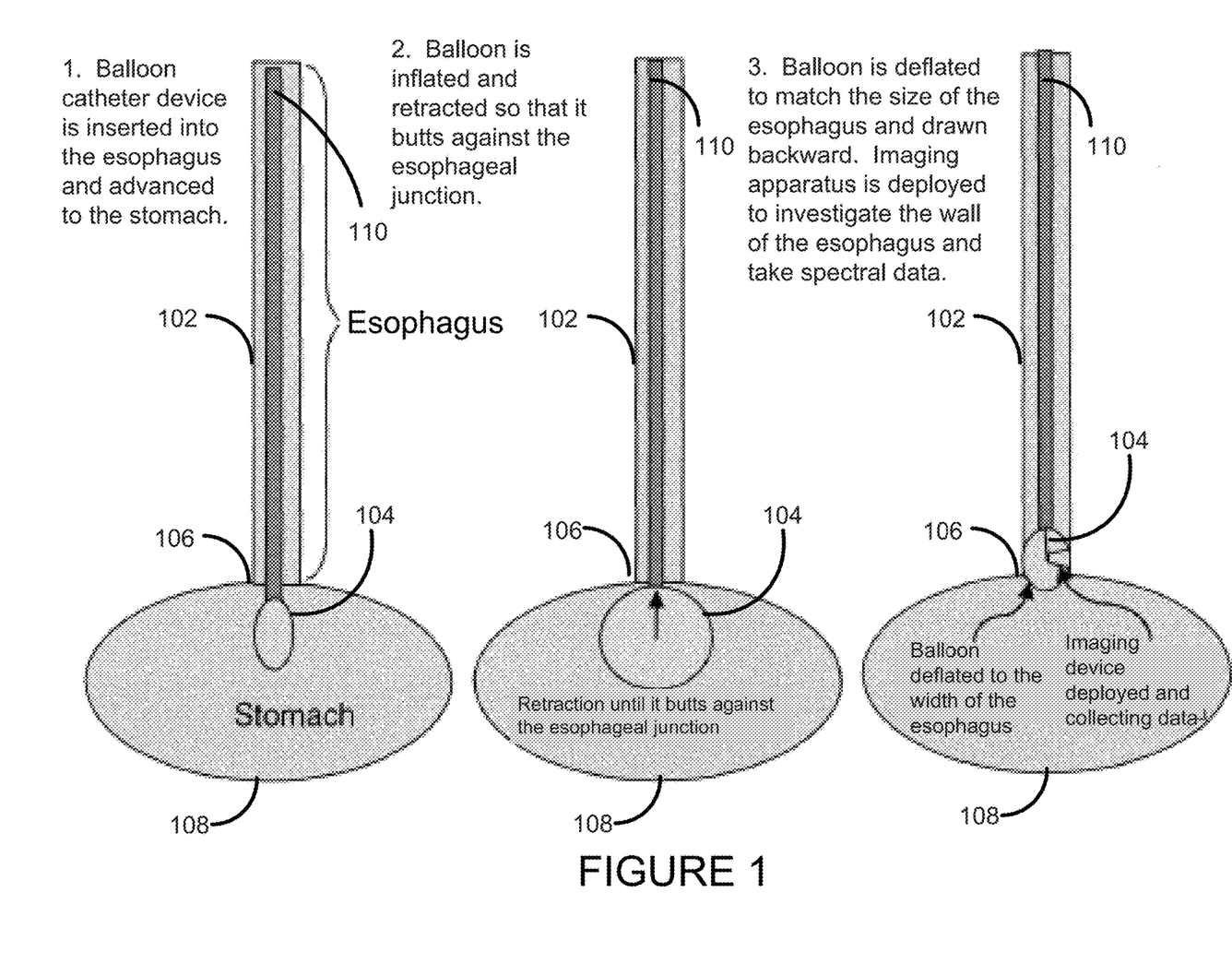
FIG. 1 shows one embodiment of the invention which allows for investigation of the esophageal wall.

FIG. 1 shows a use for the device in the detection of Barrett's esophagus 102. In this embodiment, the balloon 104 is inflated to a large size and pulled back to seat the balloon 104 at the gastroesophogeal junction 106. Initial images will by definition be taken at the gastroesophageal junction 106. The balloon 104 is then deflated to permit withdrawal and maintained at a given pressure which can be automatically adjusted or recorded and used as a portion of the information used for diagnosis. The remainder of the esophagus can be visualized and balloon pressure recorded as the device is withdrawn. As such, the technique becomes simple, conceived to be somewhat of a combination of passing a nasogastric tube into the stomach 108 and passing a foley catheter 110 into the bladder and inflating a balloon once it is in the bladder and pulling back on it to leave the balloon and distal catheter in but withdrawing the redundant catheter. The passage of such a catheter, blowing up the balloon to seat it at the end of the esophagus 102 and then deflating the balloon 104 slightly could be performed by nursing or other trained staff and not require a physician to perform.

Alternatively, a capsule may be swallowed on a string or flexible tube and the balloon similarly deployed. Endoscopy is a physician-directed procedure both because the passage of the scope is done with sedation, because localization of pathology is based on documentation of the location at which a lesion is visualized and biopsies that are often performed can be associated with complications. Here, images would be taken on withdrawal and either correlated with marks at the patient's mouth or nose or by using localization technology such as is found in the optical computer mouse. If suction or biopsy were required, it is performed through the proximal or distal ends of the semi-rigid tube or string.

Figure 2:
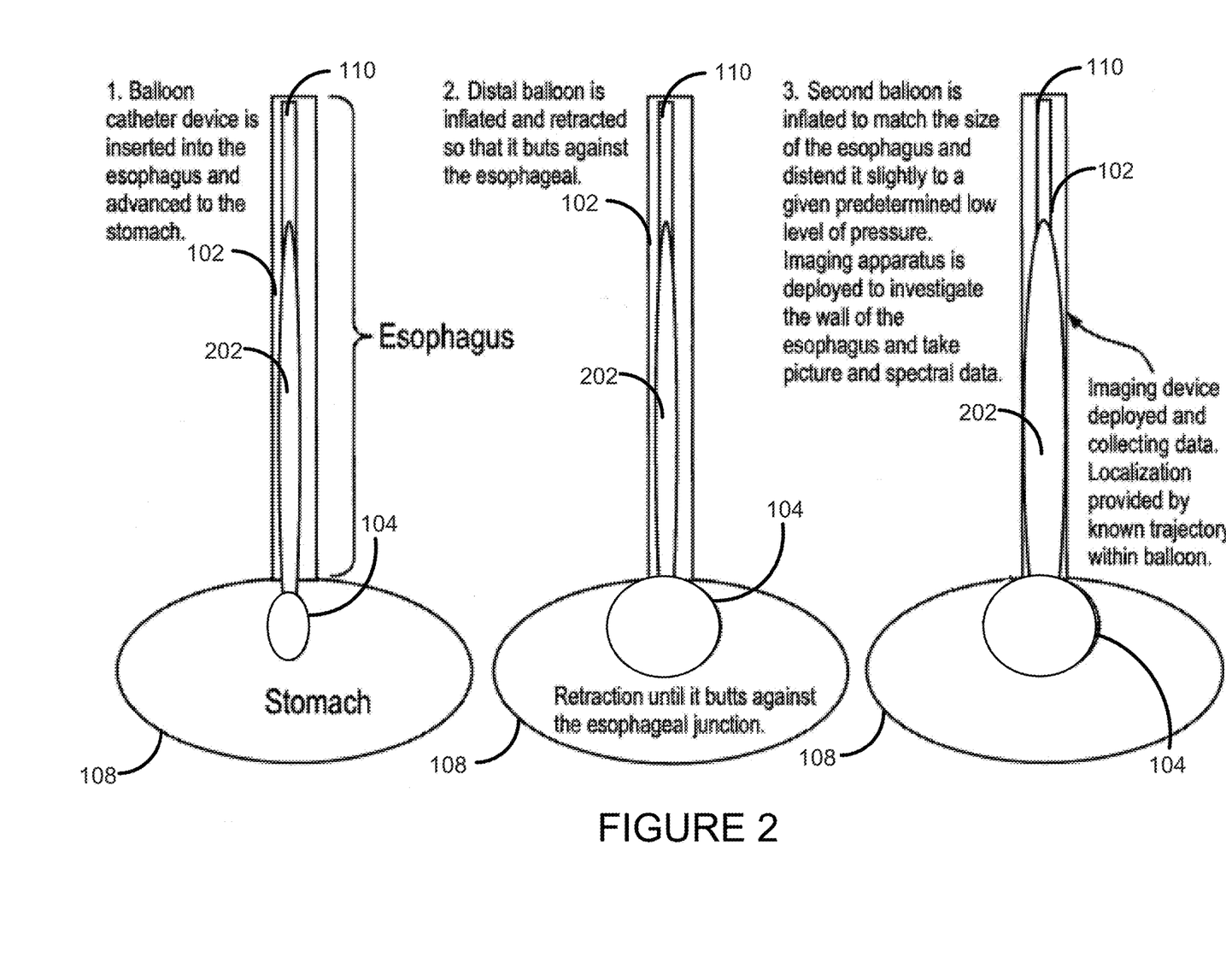
FIG. 2 shows another embodiment of the invention.

In the free capsule (FIG. 2), balloon 104 inflation is used to slow the passage of the capsule in the esophagus and to better visualize the side wall and localization could again be performed as with the optical mouse. For example, a small capsule is swallowed and immediately thereafter, the balloon is inflated from a chemical reaction or internal hydraulics, which allows better visualization and/or hyperspectral imaging or other interrogation by imaging or other conventional methods, of the side wall of the esophagus. Alternatively, the balloon could be inflated in the colon to visualize this larger structure and then deflated for excretion. The balloon is then deflated to allow for easier distal passage.

In this device is the replacement of the endoscopic tube with what is termed a string. In this instance, the string refers to a tube which is both thinner than a traditional endoscope and much less rigid. This gives the patient the ability to swallow the balloon/camera probe device.

Upon the progression of the device to the stomach (during which time there is still a substantial amount of string outside the body), the balloon can be inflated and pulled back so that is butts against the esophageal junction. This locates the bottom of the esophagus, and allows the balloon then to be deflated slightly (so that it fits in the esophagus) and images of the bottom portion of the esophagus to be captured.

The advantage of this invention is the replacement of the push of a traditional endoscope down the esophagus (which could result in tearing) with the device being pulled by the swallowing motion and the body's peristalsis, and provides more diagnostic capability in terms of choice of location for imaging than a capsule.

Another embodiment of the invention includes a device with one or more different types of balloons. The device of FIG. 2 exemplifies a second balloon 202 which can be long and would traverse a greater area of the esophagus.

Balloon shape when inflated also provides useful information through its pressure and measurement of movement of the membrane based on pressure, which provides a measure of the stress/strain of the tissue, and determine tissue elasticity.

The device may also be used for treatment as well as detection, or form the crux of a diagnostic/therapeutic coupled "smart" device with an automated feed back capability. Treatment may take a few forms, and be conducted through a separate hole outside of the balloon, for example, through a distal or proximal port, such as laser surgery, injection of chemicals/drugs, tissue removal, application of patches, etc.; with excisional biopsy using forceps; with photodynamic therapy (irradiation with a laser). This is also possible through the balloon itself and administration of a drug/compound through a needle/syringe guided by the camera at the point of diagnosis: for example sclerosis. Any of the wavelength regimes can be used to detect cancerous lesions. Signatures can be identified in any one of these wavelength regimes associated with cancer or with precancerous conditions such as Barrett's esophagus. There is a UV fluorescence technology to identify abnormal tissues in esophagus (such as tumors and Barrett's esophagus). Visible light is good for looking at perfusion and oxygen extraction differences in tissues as can be related to physiology and pathophysiology, and NIR is good for looking at water. A number of issued U.S. Patents related to this technology include U.S. Pat. Nos. 6,603,552; 6,462,770; 5,827,190; 5,769,792; 5,647,368; 5,590,660; and 5,507,287, all of which are entirely and specifically incorporated by reference.

An advantage to a large number of fibers vs. a single or just a few fibers includes image vs. point spectroscopy. Biopsy can be taken out the end hole via a biopsy forceps or maybe proximally.

Preferred embodiments of the device include imaging cameras or chips (such as CCD or CMOS), fiber optics aimed at taking spectral information from a small region of tissue, an imaging fiber bundle that can convey spectral and spatial information, imaging cameras or chips as described herein coupled with a spectral separator in order to provide multispectral or hyperspectral information (a series of wavelength-resolved images that convey spectral information in every pixel in the image), or other combinations of fiber arrays that will deliver spectral information from multiple points on the tissue. Tissue biopsy and/or drug delivery can be performed through the channels at the end of the balloon, or potentially could be performed through the balloon itself.

Methods for using the balloon probes include: the endoscope functions within the interior of an inflated balloon; the endoscope retains the ability to use tools for biopsy, suction, flushing, wiping the balloon and other embodiments that comprise typical endoscopic procedures; this is brought about through the use of a sheath which surrounds the endoscope and allows it to retract into the balloon when the balloon is inflated; and both the cap on the balloon and the end of the endoscope itself have a valve system which opens channels in the endoscope for biopsy, suction, flushing and the like.

Figure 3:
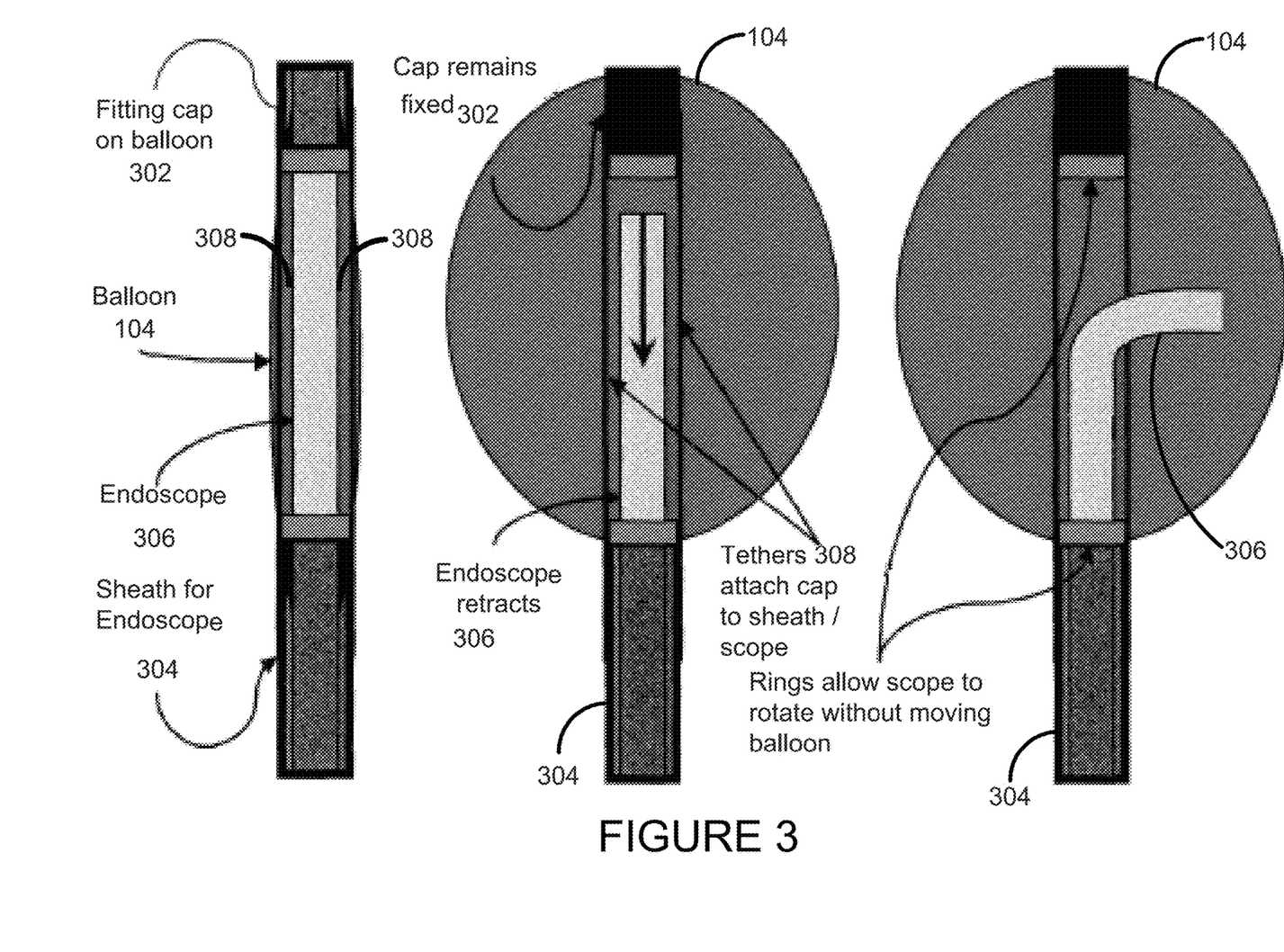
FIG. 3 shows another embodiment of the invention with a cleaning ring.

FIG. 3 shows the functioning of one embodiment of the device. Features include the cap 302 on top of the balloon 104, the balloon 104 itself, the tethers 308 that attach the cap to the sheath 304, and the endoscope 306 inside the sheath. When the balloon is inflated, the endoscope 306 is able to detach from the cap 302—which shuts the respective valves on the end of the endoscope and on the cap—and retract into to the balloon's interior. The endoscope can freely bend and rotate in the lumen of the balloon 104 and function as described herein.

Figure 4:
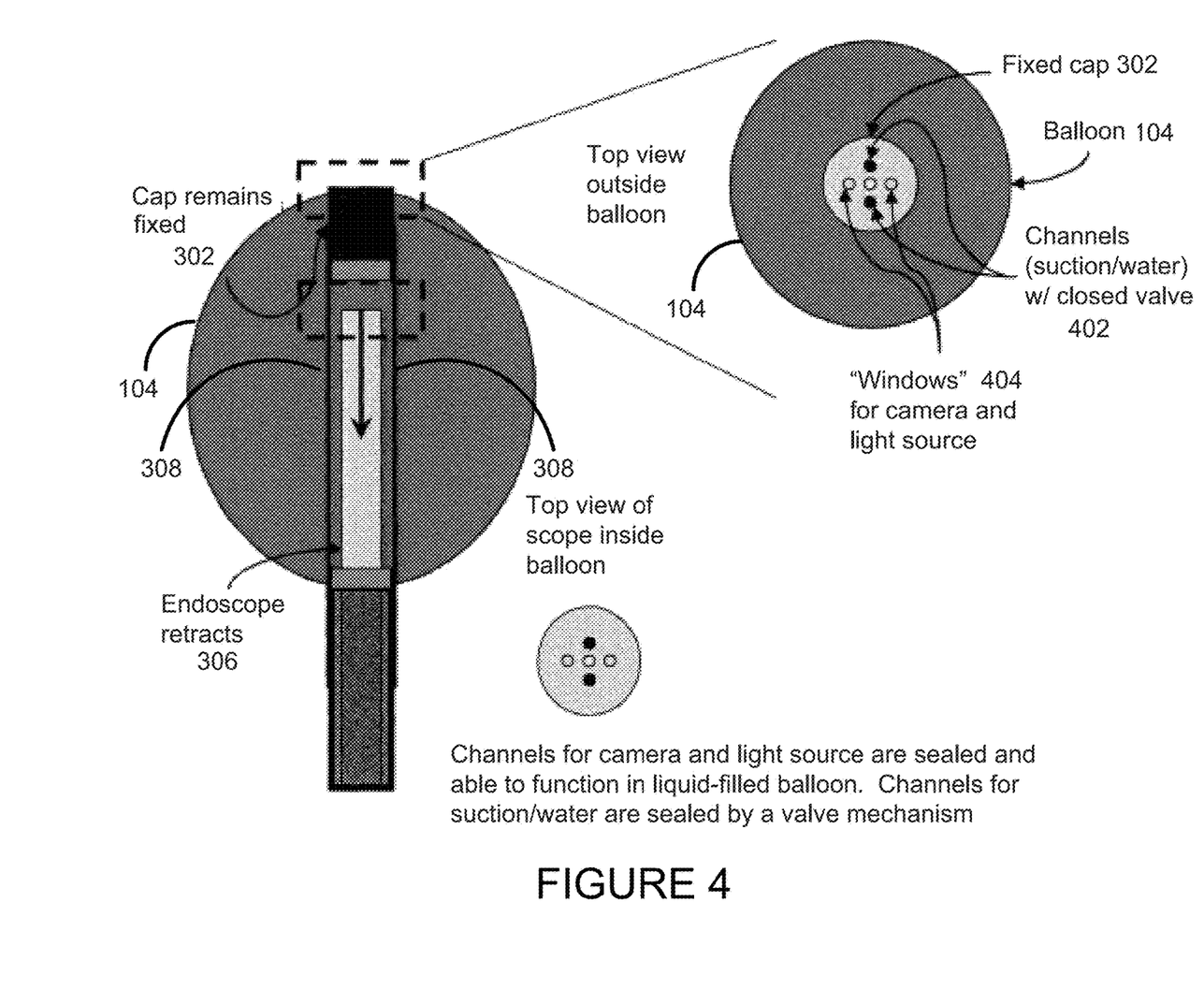
FIG. 4 shows another embodiment of the invention with a camera.

One of the features of this method is the functionality of the cap, which provides many advantages. First, the cap 302 acts as a holder for the endoscope 306 at the end of the tube/balloon. It can have a valve system (in conjunction with the end of the endoscope) that allows the channels to open and close depending on whether the endoscope in the cap or in the balloon. It can have an attachment that can serve as an optical reflectance or fluorescence standard for the calibration of the light source for the procedure. This can be important in working with hyperspectral data or other imaging or other spectral data. The cap 302 may be tethered to the sheath (by tethers inside the balloon) to allow the endoscope to rotate while inside the balloon 104 without twisting the balloon itself. The cap 302 may include windows 404 for a camera and light source.

The Valve System

Valves for suction channels on both the removable cap and on the scope itself are opened and closed by the removal or insertion of the scope into the cap 302 (see FIG. 4). The connection between cap 302 and scope 306 can be a simple twisting mechanism, such as a screw. The twisting of the mechanism to release the scope 306 from the cap 302 would close and seal all of the ports, protecting the channels 402 from the fluid inside the balloon. When disconnected, the scope itself can retract a few inches to give it room to move within the balloon. To re-attach, the scope is re-inserted into the cap and is twisted in the reverse manner. This re-twisting opens up the channels and allows for normal suction, air, and biopsy activity.

The Balloon Tethers

Figure 5:
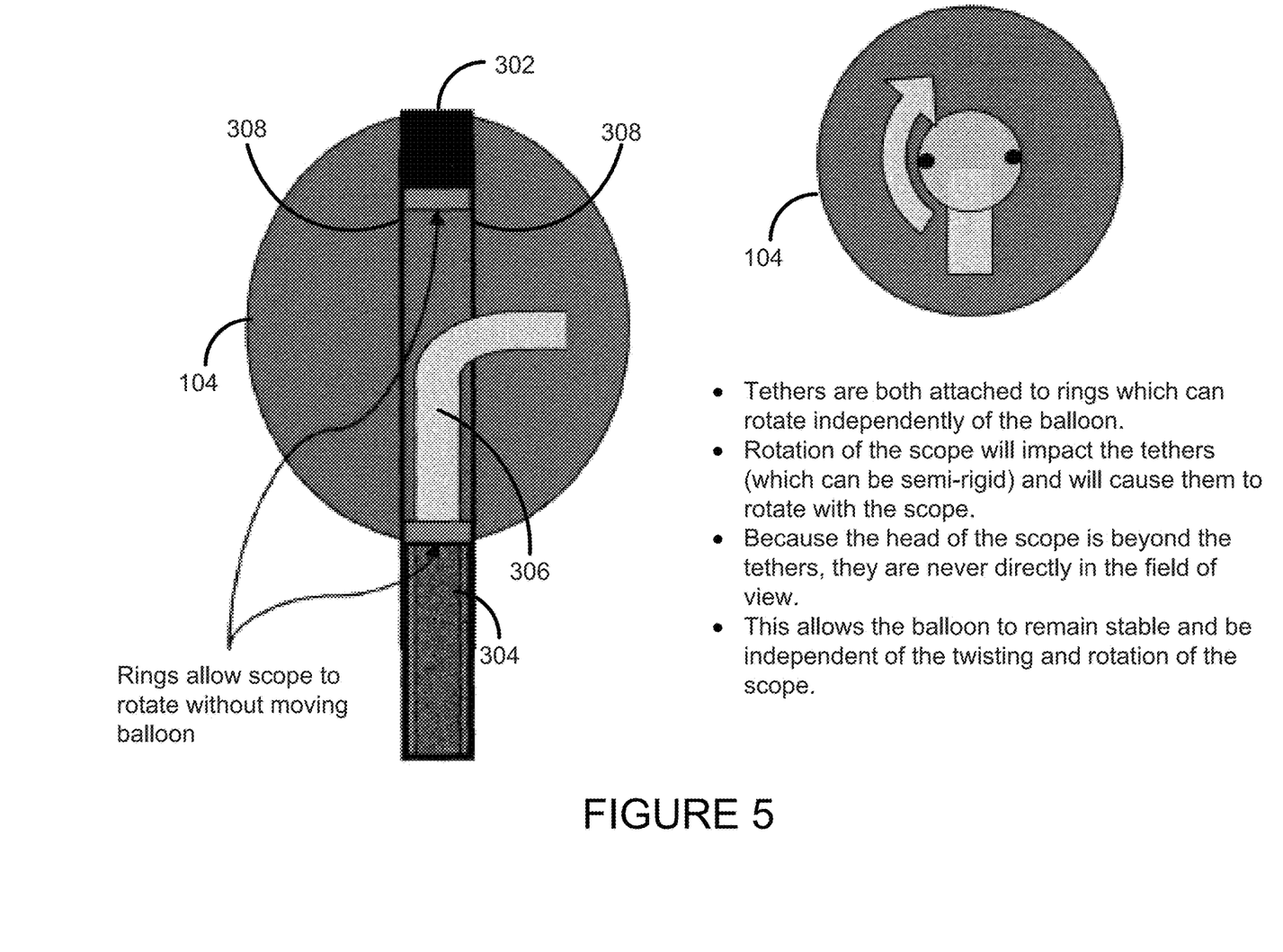
FIG. 5 shows another embodiment of the invention with which allows for rotation.
Figure 6:
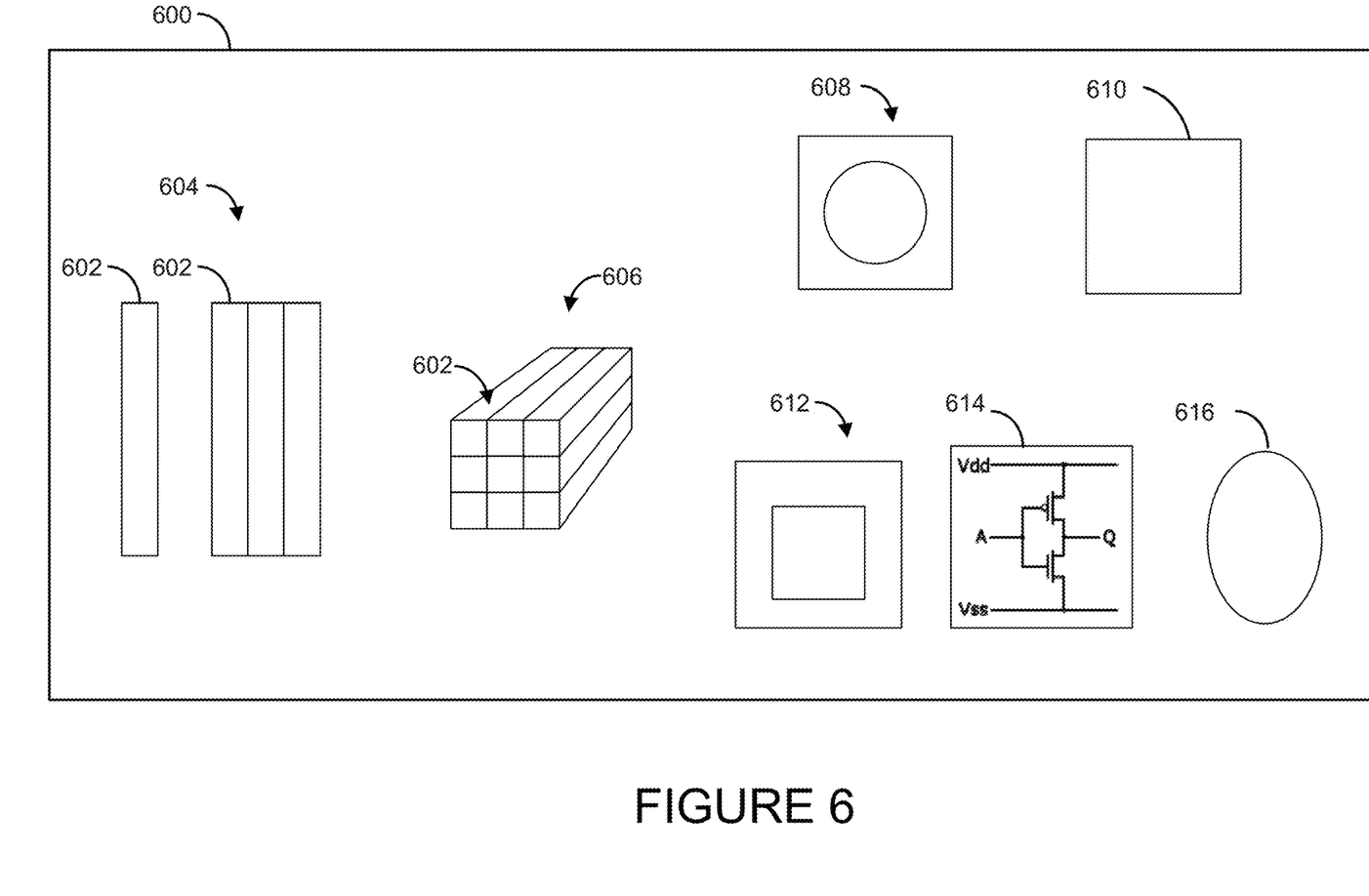
FIG. 6 shows another embodiment of the invention, a capsule 600 comprising one or more of: a fiber optic 602, a fiber bundle 604, a fiber array 606, a camera 608, a chip 610, a charge-coupled device (CCD) 612, a complementary metal-oxide-semiconductor (CMOS) 614, and a lens 616.

The balloon tethers are the portion of the device that allows the endoscope to rotate freely on the interior of the balloon when the balloon is inflated. If the device were used without a mechanism like this—with friction between the balloon and the organ/vessel wall being the only force which would keep the balloon from rotating—torque between the balloon and the sheath of the endoscope could cause the balloon to twist and fold, impairing its efficiency or utility as a device; the balloon could slide and move against the wall, producing an unstable imaging environment and potentially causing damage to the wall of the organ or vessel (see FIG. 5).

Cleaning Mechanism

The device preferably includes a method of cleaning the surface of the balloon. One embodiment of the cleaning apparatus is in the form of a tube or a strip of material that spans the length of the balloon. This "cleaning strip" is manipulated from the physician's end of the endoscope (preferably external to the body) in such a manner that the strip is dragged across the surface of the balloon, clearing any debris off of the surface.

The cleaning strip may either be impregnated with a wetting agent or other hydrating material. It may also be flushed with the same fluid used for flushing through the end of the endoscope. This fluid can be used to wash the debris off the surface of the balloon or the target tissue, possibly in conjunction with the physical scraping of the cleaning strip.

Another embodiment of the cleaning method involves channels containing the same flushing solution used in the endoscope carrying fluid through the sheath of the endoscope to the surface of the balloon. Various embodiments include devices wherein the balloon is deflated and flushed by channels running along the outside of the balloon. Another embodiment involves the cap on the end of the balloon, wherein the endoscope is re-inserted into the cap and could use the channel used for flushing external surfaces. This is re-directed by the cap to flow over the surface of the balloon. This is accomplished by modifying the cap's valve system.

Other embodiments and uses of the invention will be apparent to those skilled in the art from consideration of the specification and practice of the invention disclosed herein. All references cited herein, including all publications, U.S. and foreign patents and patent applications and U.S. Pat. No. 6,741,884, are specifically and entirely incorporated by reference. It is intended that the specification and examples be considered exemplary only.

The invention claimed is:

1. A medical device comprising: an expandable capsule that can be swallowed by a patient and positioned to a target tissue within the patient by peristalsis of the patient's digestive track; an endoscope attached to said capsule for obtaining an image of said target tissue at a wavelength of interest, wherein the capsule collects multispectral or hyperspectral information; and a thin tube or wire located at the proximal end of said capsule, the thin tube or wire configured to position said capsule to said target tissue by retraction of the thin tube or wire, wherein the thin tube or wire does not include a structure capable of being advanced forward by an operator, wherein the expandable capsule comprises a fixed cap for holding the endoscope, the fixed cap comprising one or more channels operable by a valve system at least partially contained within the proximal end of the endoscope.

2. The device of claim 1, wherein the capsule is swallowed in stages to position said device at different locations within the gastrointestinal tract.

3. The device of claim 1, wherein the thin tube or wire delivers electromagnetic radiation for visualization or illumination of the target tissue.

4. The device of claim 3, wherein the electromagnetic radiation is selected from the group consisting of visible radiation, ultraviolet radiation, near-infrared radiation, infrared radiation, and a combination thereof.

5. The device of claim 1, wherein the medical device comprises the thin tube and wherein the thin tube provides suction of secretions located proximally or distally to the capsule.

6. The device of claim 1, wherein the medical device comprises the thin tube and wherein the thin tube secretes a saline solution to clean a surface of the target tissue or of the capsule.

7. The device of claim 1, wherein the capsule comprises a fiber optic, a fiber, bundle, a fiber array, a camera, a chip, or a combination thereof that collects spectral information from one or more points on the target tissue.

8. The device of claim 1, wherein the capsule comprises a charge-coupled device (CCD), a complementary metal-oxide-semiconductor (CMOS) or a lens.

9. The device of claim 1, wherein the endoscope collects reflected or emitted radiation from the target tissue.

10. The device of claim 9, wherein the reflected or emitted radiation is selected from the group consisting of visible radiation, ultraviolet radiation, near-infrared radiation, infrared radiation, fluorescent radiation, and a combination thereof.

11. The device of claim 1, wherein the capsule comprises a fluid lucent translucent to near infrared radiation, infrared radiation, visible radiation, ultraviolet radiation, fluorescent radiation, or a combination thereof.

12. The device of claim 11, wherein the fluid is selected from the group consisting of water, water vapor, a noble gas, carbon dioxide, nitrogen, oxygen, helium, hydrogen, argon, boron, and a combination thereof.

13. The device of claim 1, wherein the expandable capsule is composed of a material that is lucent translucent to near-infrared radiation, infrared radiation, visible radiation, ultraviolet radiation, fluorescent radiation, or a combination thereof.

14. The device of claim 13, wherein the expandable capsule is infused with a substance or a drug that can be transferred to the target tissue.

15. The device of claim 14, wherein the type or dose of the substance or the drug is determined by spectral, hyperspectral or multispectral information collected by the endoscope from the target tissue.

16. The device of claim 13, wherein the expandable capsule is inflatable by a chemical reaction or by internal hydraulics.

17. The device of claim 13, wherein the expandable capsule provides a measure of stress or strain on the target tissue.

18. The device of claim 1, wherein the valve system allows the one or more channels to open and close depending on a position of the endoscope.

19. The device of claim 1, wherein the endoscope is able to bend and rotate in a lumen of the expandable capsule when detached from the fixed cap.

\* \* \* \* \*